United States Patent
Addison et al.

(10) Patent No.: US 10,463,292 B2
(45) Date of Patent: Nov. 5, 2019

(54) SYSTEM AND METHOD FOR IDENTIFYING AUTOREGULATION ZONES

(71) Applicant: COVIDIEN LP, Mansfield, MA (US)

(72) Inventors: Paul Stanley Addison, Edinburgh (GB); James N. Watson, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 414 days.

(21) Appl. No.: 15/293,610

(22) Filed: Oct. 14, 2016

(65) Prior Publication Data

US 2017/0105672 A1    Apr. 20, 2017

Related U.S. Application Data

(60) Provisional application No. 62/242,715, filed on Oct. 16, 2015.

(51) Int. Cl.
*A61B 5/00* (2006.01)
*A61B 5/1455* (2006.01)
(Continued)

(52) U.S. Cl.
CPC ............ *A61B 5/4076* (2013.01); *A61B 5/021* (2013.01); *A61B 5/0205* (2013.01);
(Continued)

(58) Field of Classification Search
CPC . A61B 5/4076; A61B 5/02028; A61B 5/0205; A61B 5/021; A61B 5/0261;
(Continued)

(56) References Cited

U.S. PATENT DOCUMENTS

| 4,776,339 A | 10/1988 | Schreiber |
| 5,351,685 A | 10/1994 | Potratz |

(Continued)

FOREIGN PATENT DOCUMENTS

| EP | 615723 A1 | 9/1994 |
| WO | WO9843071 A1 | 10/1998 |

(Continued)

OTHER PUBLICATIONS

Xu et al., "Survey of Clustering Algorithms", IEEE, TNN, vol. 16, No. 3, pp. 645-678, 2005.*

(Continued)

*Primary Examiner* — Eric F Winakur
*Assistant Examiner* — Darin M Janoschka
(74) *Attorney, Agent, or Firm* — Shumaker & Sieffert, P.A.

(57) ABSTRACT

A system configured to monitor autoregulation includes a medical sensor configured to be applied to a patient and to generate a regional oxygen saturation signal. The system includes a controller having a processor configured to receive the regional oxygen saturation signal and a blood pressure signal and to determine a cerebral oximetry index (COx) based on the blood pressure signal and the regional oxygen saturation signal. The processor is also configured to apply a data clustering algorithm to cluster COx data points over a range of blood pressures, identify a first cluster of COx data points that corresponds to an intact autoregulation zone for the patient, and provide a first output indicative of the intact autoregulation zone for the patient.

20 Claims, 4 Drawing Sheets

(51) Int. Cl.

| | |
|---|---|
| A61B 5/02 | (2006.01) |
| A61B 5/026 | (2006.01) |
| A61B 5/0205 | (2006.01) |
| A61B 5/021 | (2006.01) |
| G16H 50/20 | (2018.01) |
| G16H 40/63 | (2018.01) |
| G16H 50/30 | (2018.01) |
| G16H 20/40 | (2018.01) |

(52) U.S. Cl.
CPC ........ *A61B 5/02028* (2013.01); *A61B 5/0261* (2013.01); *A61B 5/14551* (2013.01); *A61B 5/14553* (2013.01); *A61B 5/4064* (2013.01); *A61B 5/6801* (2013.01); *A61B 5/7264* (2013.01); *A61B 5/7275* (2013.01); *G16H 20/40* (2018.01); *G16H 40/63* (2018.01); *G16H 50/20* (2018.01); *G16H 50/30* (2018.01)

(58) Field of Classification Search
CPC ............ A61B 5/14551; A61B 5/14553; A61B 5/4064; A61B 5/6801; A61B 5/7264; A61B 5/7275; G16H 50/20; G06F 19/00
See application file for complete search history.

(56) References Cited

U.S. PATENT DOCUMENTS

| | | | |
|---|---|---|---|
| 5,482,034 A | 1/1996 | Lewis et al. | |
| 5,533,507 A | 7/1996 | Potratz | |
| 5,577,500 A | 11/1996 | Potratz | |
| 5,584,296 A | 12/1996 | Cui et al. | |
| 5,626,140 A | 5/1997 | Feldman et al. | |
| 5,803,910 A | 9/1998 | Potratz | |
| 5,934,277 A | 8/1999 | Mortz | |
| 6,385,471 B1 | 5/2002 | Mortz | |
| 6,438,399 B1 | 8/2002 | Kurth | |
| 6,453,183 B1 | 9/2002 | Walker | |
| 6,505,060 B1 | 1/2003 | Norris | |
| 6,510,329 B2 | 1/2003 | Heckel | |
| 6,599,251 B2 | 7/2003 | Chen et al. | |
| 6,668,182 B2 | 12/2003 | Hubelbank | |
| 6,714,803 B1 | 3/2004 | Mortz | |
| 6,754,516 B2 | 6/2004 | Mannheimer | |
| 6,896,661 B2 | 5/2005 | Dekker | |
| 6,987,994 B1 | 1/2006 | Mortz | |
| 7,001,337 B2 | 2/2006 | Dekker | |
| 7,221,969 B2 | 5/2007 | Stoddart et al. | |
| 7,268,873 B2 | 9/2007 | Sevick-Muraca et al. | |
| 7,744,541 B2 | 6/2010 | Baruch et al. | |
| 8,556,811 B2 | 10/2013 | Brady | |
| 2004/0097797 A1 | 5/2004 | Porges et al. | |
| 2005/0004479 A1 | 1/2005 | Townsend et al. | |
| 2005/0033129 A1 | 2/2005 | Edgar, Jr. et al. | |
| 2005/0192488 A1 | 9/2005 | Bryenton et al. | |
| 2005/0192493 A1 | 9/2005 | Wuori | |
| 2007/0004977 A1 | 1/2007 | Norris | |
| 2007/0049812 A1 | 3/2007 | Aoyagi et al. | |
| 2008/0081974 A1 | 4/2008 | Pav | |
| 2008/0146901 A1 | 6/2008 | Katura et al. | |
| 2008/0200785 A1 | 8/2008 | Fortin | |
| 2008/0228053 A1 | 9/2008 | Wang et al. | |
| 2009/0326386 A1 | 12/2009 | Sethi et al. | |
| 2010/0010322 A1* | 1/2010 | Brady | A61B 5/02028 600/301 |
| 2010/0030054 A1* | 2/2010 | Baruch | A61B 5/02007 600/368 |
| 2010/0049082 A1 | 2/2010 | Hu et al. | |
| 2011/0046459 A1 | 2/2011 | Zhang et al. | |
| 2011/0105912 A1 | 5/2011 | Widman et al. | |
| 2012/0149994 A1 | 6/2012 | Luczyk et al. | |
| 2012/0253211 A1 | 10/2012 | Brady et al. | |
| 2012/0271130 A1 | 10/2012 | Benni | |
| 2013/0190632 A1 | 7/2013 | Baruch et al. | |
| 2014/0073888 A1 | 3/2014 | Sethi et al. | |
| 2014/0073930 A1* | 3/2014 | Sethi | A61B 5/02007 600/473 |
| 2014/0275818 A1 | 9/2014 | Kassem et al. | |
| 2014/0278285 A1 | 9/2014 | Marmarelis et al. | |
| 2016/0106372 A1 | 4/2016 | Addison et al. | |
| 2016/0324425 A1 | 11/2016 | Addison et al. | |
| 2016/0345913 A1 | 12/2016 | Montgomery et al. | |
| 2016/0367197 A1 | 12/2016 | Addison et al. | |
| 2017/0000395 A1 | 1/2017 | Addison et al. | |
| 2017/0000423 A1 | 1/2017 | Addison et al. | |
| 2017/0095161 A1 | 4/2017 | Addison et al. | |
| 2017/0105631 A1 | 4/2017 | Addison et al. | |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | 2016182853 A1 | 11/2016 |
| WO | WO2016182853 A1 | 11/2016 |

OTHER PUBLICATIONS

Mendelson, "Pulse Oximetry", Wiley Encyclepedia of Biomedical Engineering, pp. 1-18, 2006.*

Panerai et al., "Assessment of Cerebral Pressure Autoregulation in Humans", Physiol Meas 19 305, pp. 305-338, 1998.*

Hori et al., "Arterial Pressure Above the Upper CA Autoregulation Limit is Associated with Postoperative Delirium", BJA 113 6, pp. 1009-1017, 2014.*

Montgomery, Dean, et al.: "Data cluestering methods for the determination of cerebral autoregulation functionality," Journal of Clinical Monitoring and Computing, vol. 30, No. 5, Sep. 16, 2015, pp. 661-668.

International Search Report and Written Opinion for PCT Application No. PCT/US2016/056966 dated Jan. 20, 2017, pp. 12.

Addison, P. S., et al.; "Low-Oscillation Complex Wavelets," Journal of Sound and Vibration, 2002, vol. 254, Elsevier Science Ltd., pp. 1-30.

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," *Physiol. Meas.*, vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.

(56) References Cited

OTHER PUBLICATIONS

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "Is respiration-induced variation in the photoplethysmogram associated with major hypovolemia in patients with actue tramatic injuries," Shock, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

Czosnyka, Marek, et al.; "Monitoring of cerebrovascular autoregulation: Facts, Myths, and Missing Links," Neurocrit Care (2009) 10:373-386.

Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.

Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.

Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.

Ge, Z., "Significance tests for the wavelet cross spectrum and wavelet linear coherence," Annales Geophysicae, 2008, 26, Copernicus Publications on behalf of European Geosciences Union, pp. 3819-3829.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Goldman, Julian M.; "Masimo Signal Extraction Pulse Oximetry," *Journal of Clinical Monitoring and Computing*, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.

Hamilton, Patrick S., et al.; "Effect of Adaptive Motion-Artifact Reduction on QRS Detection," *Biomedical Instrumentation & Technology*, pp. 197-202 (May-Jun. 2000).

Huang, J., et al.; "Low Power Motion Tolerant Pulse Oximetry," Anesthesia & Analgesia 2002 94: S103.

Johansson, A.; "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform for pulse oximetry," pp. II-310-II-311 (2001).

Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lee, Jennifer K., et al.; A pilot study of cerebrovascular reactivity autoregulation after pediatric cardiac arrest, Resuscitation 85, 2014, Elsevier Ireland Ltd., pp. 1387-1393.

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

Morren, G., et al.; "Detection of autoregulation in the brain of premature infants using a novel subspace-based technique," 23rd Annual International Conference of IEEE Engineering in Medicine and Biology Society, Oct. 2001; pp. 1-4.

Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.

Neumann, R., et al.; "Fourier Artifact suppression Technology Provides Reliable $SpO_2$," Anesthesia & Analgesia 2002, 94: S105.

Obrig, Hellmuth, et al.; "Spontaneous low frequency oscillations of cerebral heodynamics and metabolism in human adults," NeuroImage 12, 623-639 (2000).

Odagiri, Y.; "Pulse Wave Measuring Device," *Micromechatronics*, vol. 42, No. 3, pp. 6-11 (published Sep. 1998) (Article in Japanese—contains English summary of article).

Ono, Masahiro, et al.; "Validation of a stand-alone near-infrared spectroscopy system for monitoring cerebral autoregulaiton during

(56) References Cited

OTHER PUBLICATIONS cardiac surgery," International Anethesia Research Society, Jan. 2013, vol. 116, No. 1, pp. 198-204.
Panerai, B.; "Cerebral Autoregulation: from models to clinical Applications," Cardiovascular Engineering: an International Journal, vol. 8, No. 1, Nov. 28, 2007, (28 pgs.).
Payne, Stephen J., et al.; "Tissue Oxygenation Index as a Measure of Cerebral Autoregulation," Biomedial Engineering, Feb. 2004, Innsbruck, Austria, pp. 546-550.
Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
Reinhard, Matthias, et al.; "Oscillatory cerebral hemodynamics—the macro- vs. microvascular level," Journal of the Neurological Sciences 250 (2006) 103-109.
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.
Shamir, M., et al.; "Pulse oximetry plethysmographic waveform during changes in blood volume," British Journal of Anaesthesia 82(2): 178-81 (1999).
Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.
Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.
Such, Hans Olaf; "Optoelectronic Non-invasive Vascular Diagnostics Using multiple Wavelength and Imaging Approach," *Dissertation*, (1998).
Todd, Bryan, et al.; "The Identification of Peaks in Physiological Signals," *Computers and Biomedical Research*, vol. 32, pp. 322-335 (1999).
Tsuji, Miles, et al.; "Cerebral intravascular oxygenation correlates with mean arterial pressure in critically ill premature infants," American Academy of Pediatrics, 2000; 106; pp. 625-632.
Wagner, Bendicht P., et al.; "Dynanic cerebral autoregulatory response to blood pressure rise measured by near-infrared spectroscopy and intracranial pressure," Critical Care Medicine 2002, vol. 30, No. 9, pp. 2014-2021.
Whitaker, E., et al.; "Cerebrovascular Autoregulation After Pediatric Cardiac Arrest," NEURO-85, 2012, 2 pgs.
Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.
Wong, Flora Y., et al.; "Impaired Autoregulation in preterm infants identified by using spatially resolved spectroscopy," American Academy of Pediatrics DOI:10.1542 (2008) e604-611.
Wu, Dongmei, et al.; "Na*/H* Exchange inhibition delays the onset of hypovolemic circulatory shock in pigs," Shock, vol. 29, No. 4, pp. 519-525 (2008).
Wu, et al.; "Using synchrosqueezing transform to discover breathing dynamics from ECG signals," arXiv:1105.1571, vol. 2, Dec. 2013, pp. 1-9.
Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.
Zhang, Rong, et al.; "Transfer function analysis of dynamic cerebral autoregulation in humans," 1998 the American Physiological Society; pp. H233-H241.
Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.
U.S. Appl. No. 15/648,665, filed Jul. 13, 2017, Dean Montgomery.
Chuan et al., "Is cerebrovascular autoregulation associated with outcomes after major noncardiac surgery? A prospective observational pilot study," Acta Anaesthesiol Scand., Aug. 5, 2018, 10 pp.
International Search Report and Written Opinion from International Application No. PCT/US2016/056966, dated Jan. 20, 2017, 10 pp.
U.S. Appl. No. 15/666,167, filed Aug. 1, 2017, naming inventors Addison et al.

\* cited by examiner

SYSTEM AND METHOD FOR IDENTIFYING AUTOREGULATION ZONES

CROSS-REFERENCE TO RELATED APPLICATION

This application claims the benefit of U.S. Provisional Application No. 62/242,715, filed Oct. 16, 2015, which is hereby incorporated by reference herein in its entirety.

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems and methods for monitoring autoregulation may determine a patient's autoregulation status based on various physiological signals. However, existing systems and methods for determining the patient's autoregulation status may be inefficient and/or unreliable.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
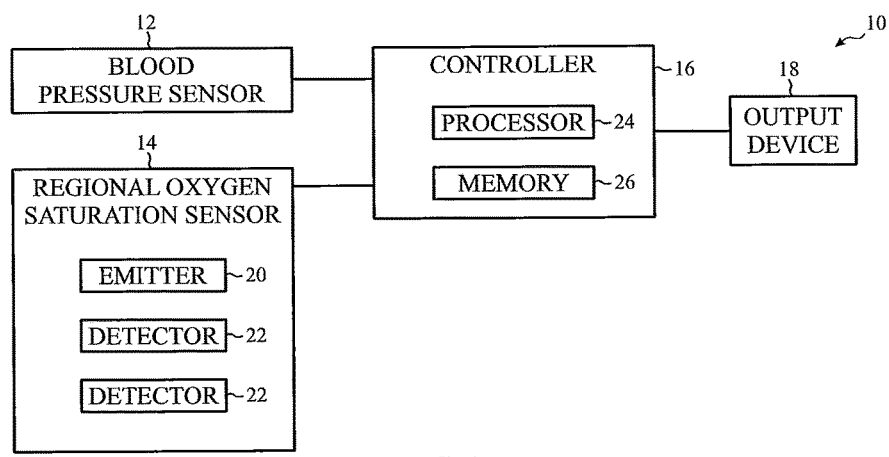
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) indicative of the patient's autoregulation status may be derived based at least in part on a linear correlation between the patient's blood pressure and oxygen saturation.

In certain situations, it may be beneficial to identify autoregulation zones indicative of a patient's blood pressure dependent autoregulation status. A patient's autoregulation system may typically function well over a certain range of blood pressures. Accordingly, each patient typically exhibits at least three autoregulation zones: a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired. For example, although the blood pressures at which the autoregulation system functions properly may vary by patient, a particular patient may exhibit a lower impaired autoregulation zone associated with relatively low blood pressures of less than approximately 60 mmHg at which the patient's autoregulation function is impaired, an intact autoregulation zone associated with intermediate blood pressures between approximately 60 and 150 mmHg at which the patient's autoregulation system works properly, and an upper impaired autoregulation zone associated with relatively high blood pressures above approximately 150 mmHg at which the patient's autoregulation function is impaired. It may be advantageous to identify the patient's autoregulation zones and/or to determine an upper limit of autoregulation (ULA) value and/or a lower limit of autoregulation (LLA) that approximately define an upper and a lower blood pressure (e.g., mean arterial pressure (MAP)) boundary, respectively, within which autoregulation is generally intact and functioning properly. Blood pressures approximately above the ULA and/or approximately below the LLA may be associated with impaired autoregulation function. In some cases, identifying the ULA, LLA, autoregulation zones, and/or the patient's autoregulation status using typical systems and methods may be inefficient and/or unreliable.

Accordingly, systems and methods for efficiently and/or reliably identifying the ULA, LLA, and/or blood pressures associated with the autoregulation zones, and thereby enabling efficient and/or reliable determination of the patient's autoregulation status, are provided herein. Furthermore, in some embodiments, the systems and methods may be configured to determine a target blood pressure for the patient. In some embodiments, the target blood pressure may be a blood pressure value or a range of blood pressure values within the intact autoregulation zone. The target blood pressure may represent a blood pressure value or a range of values at which the patient's autoregulation function is greatest and/or may be useful for clinical management of a patient's blood pressure. For example, the target blood pressure may guide a healthcare provider's treatment of the patient (e.g., provide an indication of whether the healthcare provider should administer medication to lower the patient's blood pressure or to raise the patient's blood pressure to reach the target blood pressure within the intact autoregulation zone). As discussed in more detail below, the systems and methods may be configured to utilize one or more data clustering algorithms to facilitate identification of the autoregulation zone(s) and/or the target blood pressure. In some embodiments, the system may be configured to provide information indicative of the autoregulation zones, the autoregulation status, and/or the target blood pressure to an operator. Such systems and methods may in turn provide improved patient monitoring and patient care.

FIG. 1 is a block diagram of an embodiment of a system 10 for monitoring a patient's autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., mean arterial blood pressure (MAP)). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable identification of the autoregulation zone(s) and to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. The emitter 20 may be driven to emit light by light drive circuitry of a monitor (e.g., a specialized monitor having a controller configured to control the light drive circuitry). In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 20. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed. Surface data (e.g., from the skin) may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status. While the depicted oxygen saturation sensor 14 is a regional saturation sensor, the sensor 14 may be a pulse oximeter configured to obtain the patient's oxygen saturation or may be any suitable sensor configured to provide a signal indicative of the patient's blood flow. For example, the sensor 14 may be configured to emit light at a single wavelength (e.g., an isobestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to determine the autoregulation zone(s) and/or to evaluate the patient's cerebral autoregulation status. In some embodiments, the controller 16 may be part of a specialized monitor and/or may be configured to control operation of (e.g., control light drive circuitry to drive the emitter 20 of the oxygen saturation sensor 14) and/or receive signals directly from the blood pressure sensor 12 and/or the oxygen saturation sensor 14. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

Figure 2:
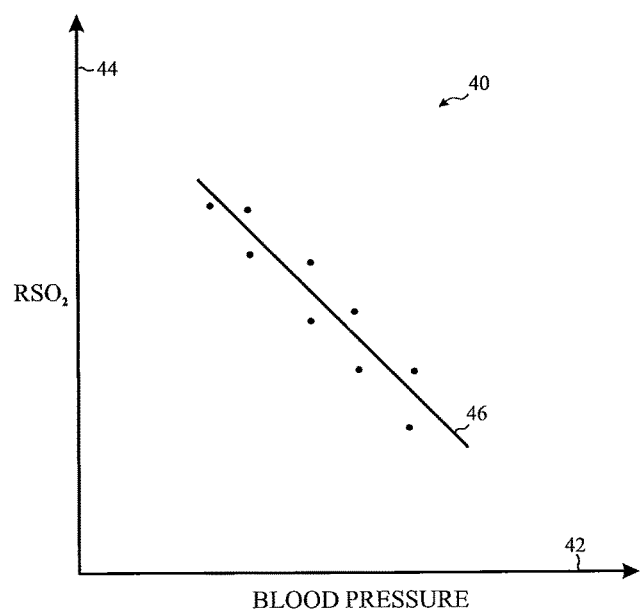
FIG. 2 is an example of a graph illustrating a linear correlation between oxygen saturation values and blood pressure values.

In some embodiments, the controller 16 may be configured to determine a cerebral oximetry index (COx) based on the blood pressure signal and the oxygen saturation signal. The COx is generally indicative of vascular reactivity, which is related to cerebral blood vessels' ability to control proper blood flow, via vasoconstriction (a narrowing of the blood vessel) and/or vasodilation (expansion of the blood vessel), for example. The controller 16 may derive a COx value by determining a linear correlation between blood pressure measurements and oxygen saturation measurements. With the foregoing in mind, FIG. 2 is an example of a graph 40 illustrating a linear correlation between blood pressure measurements 42 (e.g., arterial blood pressure measurements) and oxygen saturation measurements 44. The linear correlation may be based on a Pearson coefficient, for example. The Pearson coefficient may be defined as the covariance of the measured blood pressure (e.g., arterial blood pressure) and oxygen saturation divided by the product of their standard deviations. The result of the linear correlation may be a regression line 46 between the blood pressure measurements 42 and the oxygen saturation measurements 44, and the slope of the regression line 46 may be generally indicative of the patient's autoregulation status. In the illustrated example, the slope of the regression line 46 is negative and, thus, the COx value is between −1 and 0. However, when the regression line 46 has a positive slope, the COx value is between 0 and 1.

In some embodiments, the controller 16 may be configured to utilize the COx values to efficiently identify various autoregulation zones and/or blood pressures associated with various autoregulation zones (e.g., a lower impaired autoregulation zone associated with relatively low blood pressures at which the patient's autoregulation function is impaired, an intact autoregulation zone associated with intermediate blood pressures at which the patient's autoregulation system works properly, and an upper impaired autoregulation zone associated with relatively high blood pressures at which the patient's autoregulation function is impaired). Identifying the various autoregulation zones may, in turn, facilitate determination of the patient's autoregulation status.

Figure 3:
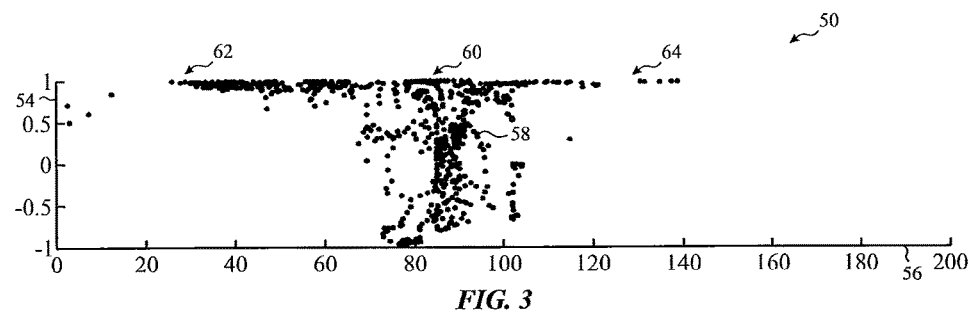
FIG. 3 is an example of a graph illustrating cerebral oximetry index (COx) plotted against mean arterial pressure (MAP)

FIG. 3 is an example of a graph 50 illustrating the COx 54 plotted against blood pressure 56 (e.g., mean arterial pressure (MAP)). In particular, the graph 50 of FIG. 3 illustrates individual raw data points 58. As shown, the data points 58 are distributed (e.g., spread) across COx values 54 in a characteristic manner at the various blood pressures 56. In particular, the data points 58 may have a relatively greater spread across COx values 54 at intermediate blood pressures associated with an intact autoregulation zone 60. Additionally, the data points 58 may have a relatively lower spread across COx values 54 at lower blood pressures associated with a lower impaired autoregulation zone 62 and at higher blood pressures associated with a higher impaired autoregulation zone 64. Furthermore, the data points 58 may generally vary between −1 and +1 at the intermediate blood pressures associated with the intact autoregulation zone 60, and may cluster at approximately +1 at the lower blood pressures associated with the lower impaired autoregulation zone 62 and at the higher blood pressures associated with the higher impaired autoregulation zone 64. These distribution patterns and/or characteristics may be utilized to facilitate efficient and/or reliable determination of the various autoregulation zones, the LLA, the ULA, and/or a target blood pressure. For example, any of a variety of data clustering algorithms may be utilized by the controller 16 to cluster the data points 58, thereby facilitating identification of the autoregulation zones, the LLA, the ULA, and/or a target blood pressure, as discussed in detail below.

Returning to FIG. 1, in the illustrated embodiment, the controller 16 includes a processor 24 and a memory device 26. The controller 16 may also include one or more storage devices. As discussed in more detail below, the processor 24 may be used to execute code stored in the memory device 26 or other suitable computer-readable storage medium or memory circuitry, such as code for implementing various monitoring functionalities. The processor 24 may be used to execute software, such as software for carrying out any of the techniques disclosed herein, such as processing the blood pressure signals and/or oxygen saturation signals, determining a COx value, applying a data clustering algorithm to the data points 58, identifying autoregulation zones, identifying the LLA and/or the ULA, determining a target blood pressure, causing display of information related to autoregulation zones and/or status on a display, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for processing the blood pressure signals and/or oxygen saturation signals, determining a COx value, applying the data clustering algorithm, identifying autoregulation zones, identifying the LLA and/or the ULA, determining a target blood pressure, causing display of information related to autoregulation zones and/or status on a display, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the COx, the target blood pressure, etc.), instructions (e.g., software or firmware for processing the blood pressure signals and/or oxygen saturation signals, determining a COx value, applying the data clustering algorithm, identifying autoregulation zones, identifying the LLA and/or the ULA, determining the target blood pressure, causing display of information related to autoregulation zones and/or status on a display, and so forth), predetermined thresholds, and any other suitable data.

As shown, the system 10 includes the output device 18. In some embodiments, the controller 16 may be configured to provide signals indicative of the autoregulation zones and/or the patient's autoregulation status to the output device 18. In some embodiments, the controller 16 may be configured to provide signals indicative of the target blood pressure to the output device 18. As discussed in more detail below, the controller 16 may be configured to generate an alarm signal indicative of the patient's autoregulation status and to provide the alarm signal to the output device 18. The output device 18 may include any device configured to receive signals (e.g., signals indicative of the autoregulation zones, the patient's autoregulation status, the target blood pressure, the alarm signal, or the like) from the controller 16 and visually and/or audibly output information indicative of the patient's autoregulation status (e.g., the COx, the autoregulation zones, the target blood pressure, an alarm, a text message, a color, or the like). For instance, the output device 18 may include a display configured to provide a visual representation of the patient's autoregulation status, autoregulation zones, the target blood pressure, and/or the COx as determined by the controller 16. Additionally or alternatively, the output device 18 may include an audio device configured to provide sounds (e.g., spoken message, beeps, or the like) indicative of the patient's autoregulation status, the COx, the target blood pressure, and/or the autoregulation zones. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a specialized computer or monitor).

Figure 4:
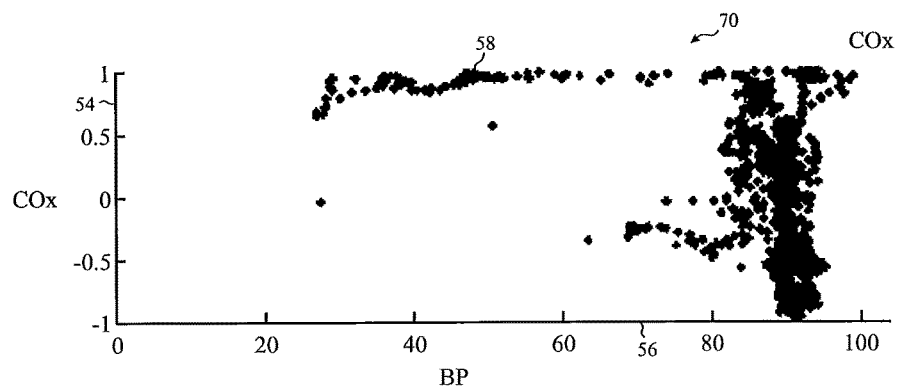
FIG. 4 is another example of a graph illustrating COx plotted against MAP.

FIG. 4 is another example of a graph 70 illustrating the COx 54 plotted against blood pressure 56 (e.g., mean arterial pressure (MAP)). To facilitate discussion, the graph 70 includes individual raw data points 58 at blood pressures below approximately 100 mmHg. It should be understood that the techniques (e.g., clustering techniques) disclosed herein may be adapted to identify the various autoregulation zones across any suitable range of blood pressures, the LLA, and/or the ULA. In some embodiments, the controller 16 may be configured to provide a suitable picture, representation, and/or image depicting the data points 58 (e.g., the graph 70) on a display (e.g., via the output device 18).

Figure 5:
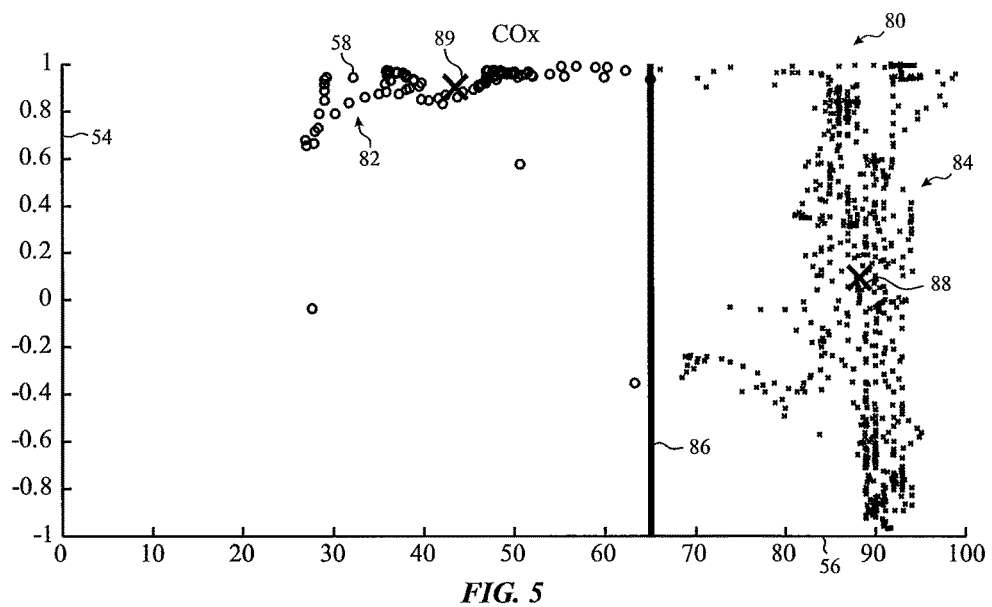
FIG. 5 illustrates the graph of FIG. 4 after application of a k-means clustering algorithm.

FIG. 5 is an example of a graph 80 illustrating application of a k-means clustering algorithm to the data points 58 of the graph 70 of FIG. 4. To generate the graph 80, the k-means clustering algorithm is applied (e.g., by the controller 16) to the raw data points 58 without or prior to data binning (e.g., without or prior to grouping the raw data points 58 into a smaller number of bins or blood pressure intervals). As shown, application of the k-means clustering algorithm to the data points 58 may result in a first cluster 82 associated with lower blood pressures and a second cluster 84 associated with higher blood pressures. In the illustrated graph 80, each of the data points 58 within the first cluster 82 are represented by circles, and each of the data points 58 within the second cluster 84 are represented by crosses. The controller 16 may evaluate the clusters 82, 84 (e.g., evaluate blood pressures within the clusters 82, 84, etc.) to determine that the first cluster 82 corresponds to the lower impaired autoregulation zone 62, and the second cluster 84 corresponds to the intact autoregulation zone 60, in the illustrated embodiment. Furthermore, the controller 16 may determine a boundary 86 between the clusters 82, 84, and may determine that the boundary 86 corresponds to the LLA.

For example, if the application of the clustering algorithm by the controller 16 results in a first cluster at relatively low blood pressures and/or with a narrow spread of COx values and a second cluster at relatively higher blood pressures and/or with a relatively wider spread of COx values, then the controller 16 may determine that the first cluster (e.g., cluster 82) corresponds to the lower impaired autoregulation zone 62 and the second cluster (e.g., cluster 84) corresponds to the intact autoregulation zone 60. By way of another example, if application of the clustering algorithm by the controller 16 results in the detection of three clusters (e.g., a first cluster at relatively low blood pressures, a second cluster at intermediate blood pressures, and a third cluster at relatively high blood pressures), the controller 16 may determine that the first cluster corresponds to the lower impaired autoregulation zone 62, the second cluster corresponds to the intact autoregulation zone 60, and the third cluster corresponds to the higher impaired autoregulation zone 64. By way of another example, if application of the clustering algorithm by the controller 16 results in a first cluster that significantly overlaps with or includes low blood pressures that are typically associated with the lower impaired autoregulation zone (e.g., based on empirical data or historical patient data) and a second cluster that significantly overlaps with or includes intermediate blood pressures that are typically associated with the intact autoregulation zone, the controller 16 may determine that the first cluster corresponds to the lower impaired autoregulation zone 62 and that the second cluster corresponds to the intact autoregulation zone 60. For example, if the first cluster includes a blood pressure of approximately 40 mmHg and the second cluster includes a blood pressure of approximately 90 mmHg, the controller 16 may determine that the first cluster corresponds to the lower impaired autoregulation zone 62 and the second cluster corresponds to the intact autoregulation zone 60.

In some embodiments, the controller 16 may be configured to provide an output indicative of the clusters 82, 84 and/or the boundary 86. For example, in some embodiments, the controller 16 may be configured to provide the graph 80 or a similar graphical representation of the clusters 82, 84 and/or the boundary 86 on a display (e.g., via the output device 18). In some embodiments, the controller 16 may be configured to provide markers (e.g., boxes or boundaries) about each of the clusters 82, 84 on a display of the graph 80 to facilitate visualization of the clusters 82, 84 and/or the autoregulation zones derived from the clusters 82, 84 and/or the boundary 86. The controller 16 may be configured to provide a suitable picture, representation, and/or image (e.g., via the output device 18) depicting one or more of the various autoregulation zones, the LLA, and/or the ULA derived from the clusters 82, 84 and/or the boundary 86.

Determination of the clusters 82, 84 and/or the boundary 86 may enable the controller 16 to efficiently and/or reliably categorize and/or determine which autoregulation zone the patient's blood pressure falls within. In some embodiments, the controller 16 may be configured to identify blood pressures associated with each of the autoregulation zones (e.g., via application of a clustering algorithm to data points 58 to identify clusters 82, 84) based on a limited number of data points 58 without first determining the LLA or the ULA, which may require additional data points and/or may take several minutes or hours. Thus, the disclosed embodiments may enable efficient identification of the autoregulation zones, the patient's autoregulation status, and thus, may provide improved patient care and outcomes.

As shown in FIG. 5, a centroid 88 (e.g., a mean or average across all points in the cluster) of the cluster (e.g., second cluster 84) corresponding to the intact autoregulation zone 60 may be identified (e.g., by the controller 16). In some embodiments, the centroid 88 may be used (e.g., by the controller 16) to generate a target blood pressure for the patient. In some embodiments, a blood pressure value corresponding to the centroid 88 may be the target blood pressure value. In some embodiments, the target blood pressure may be a range of blood pressures about the centroid 88 (e.g., 1, 2, 3, 4, 5, or more percent about the centroid 88 or 1, 5, 10 mmHg about the centroid 88). For example, in the graph 80 of FIG. 5, the centroid 88 of the second cluster 84 corresponding to the intact is located at approximately 89 mmHg. In some embodiments, the controller 16 may determine the target blood pressure to be 89 mmHg or some range centered about 89 mmHg, such as a range of 84 to 94 mmHg, for example. The target blood pressure may represent a blood pressure value or a range of values at which the patient's autoregulation function is greatest and/or may be useful for clinical management of a patient's blood pressure.

During patient care, a healthcare provider may provide treatment (e.g., medication, changes in posture, or the like) to the patient to adjust the patient's blood pressure. The target blood pressure may be provided (e.g., by the controller 16 via the output device 18) to the healthcare provider to notify the healthcare provider of a blood pressure at which the patient's autoregulation is expected to function well or most effectively. Thus, the target blood pressure may guide a healthcare provider's treatment of the patient (e.g., provide an indication of whether the healthcare provider should administer medication to lower the patient's blood pressure, to raise the patient's blood pressure, or to stop administration of blood pressure medication to reach the target blood pressure within the intact autoregulation zone). In some embodiments, the controller 16 may be configured to provide an indication (e.g., a displayed text message or light or an audible spoken message or alarm via the output device 18) when the patient's blood pressure does not match the target blood pressure. In some embodiments, the target blood pressure and/or the blood pressures associated with each of the autoregulation zones may be provided to the controller 16, or to another suitable processing device, to facilitate control of an automated blood pressure control device configured to automatically provide treatment to the patient to adjust the patient's blood pressure toward the target blood pressure. Thus, the controller of the automated blood pressure device may cause the device to dispense a medication (e.g., via intravenous fluids) or otherwise treat the patient to adjust the patient's blood pressure based on a comparison between the patient's blood pressure and the target blood pressure. For example, the controller may cause the device to dispense the medication to increase the patient's blood pressure to the target blood pressure if the patient's blood pressure is below the target blood pressure.

In some embodiments, a centroid 89 of a cluster associated with one of the impaired autoregulation zones (e.g., the lower impaired autoregulation zone 62 or the higher impaired autoregulation zone 64) may be identified by the controller 16. A blood pressure value corresponding to the centroid 89 may be useful for clinical management of a patient's blood pressure. For example, the blood pressure value corresponding to the centroid 89 may be provided to the healthcare provider (e.g., by the controller 16 via the output device 18) and may enable the healthcare provider to evaluate the severity of the patient's autoregulation impairment. If the patient's blood pressure is below the blood pressure associated with the centroid 89 of the first cluster 82 associated with the lower impaired autoregulation zone 62, the severity of autoregulation impairment is greater than if the patient's blood pressure is above the centroid 89. In some embodiments, the controller 16 may be configured to provide an indication (e.g., a displayed text message or light or an audible spoken message or alarm via the output device 18) when the patient's blood pressure falls below the blood pressure value associated with the centroid 89.

In some embodiments, the controller 16 may automatically initiate application of the clustering algorithm to the data points 58 in response to receipt or to determination of a predetermined number of data points 58. For example, the controller 16 may automatically begin application of the clustering algorithm after about 10, 20, 30, 40, 50, 60, 70, 80, 90, 100, 200, 300, 400, 500, or more data points 58 are received or determined. In some embodiments, the controller 16 may automatically begin application of the clustering algorithm within 1, 2, 3, 4, 5, 10, 15, or 30 minutes of the beginning of the monitoring session. In some embodiments, the controller 16 may automatically re-apply the clustering algorithm or update the clusters and/or target blood pressure during the monitoring session, such as every 15, 30, 60, or 90 seconds. In some embodiments, the controller 16 may only output (e.g., via the output device 18) information related to the clusters and/or the target blood pressure once the controller 16, using the clustering algorithm, identifies at least two distinct clusters of data points 58. For example, the controller 16 may cause display of information indicative of the autoregulation zones, the clusters, the LLA, the ULA, the target blood pressure, in response to identification of at least two distinct clusters of data points 58 by the controller 16. In some embodiments, the controller 16 may cause display of information indicative of the autoregulation zones, the clusters, the LLA, the ULA, the target blood pressure in response to identification of at least two distinct clusters of data points 58, where one distinct cluster overlaps or includes a low or high blood pressure (e.g., less than 60 mmHg or more than 150 mmHg) typically associated with impaired autoregulation and where another distinct cluster overlaps or includes an intermediate blood pressure (e.g., between 60 and 150 mmHg) typically associated with intact autoregulation. Such techniques may enable the controller 16 to output reliable information related to the autoregulation status of the patient.

Figure 6:
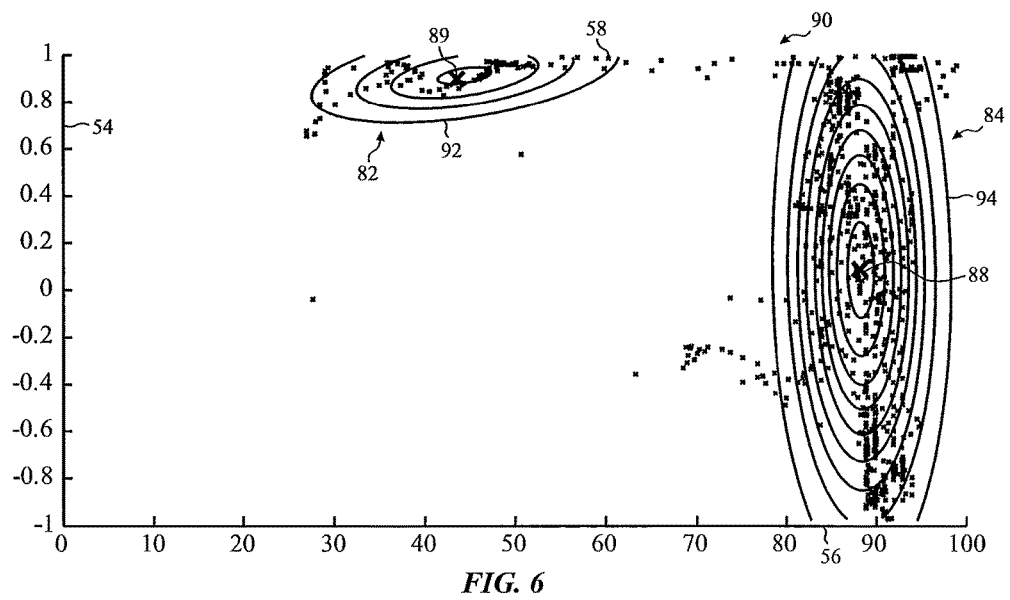
FIG. 6 illustrates the graph of FIG. 4 after application of a Gaussian mixture model.

FIG. 6 is an example of a graph 90 after application of a Gaussian mixture model to the data points 58 of the graph 70 of FIG. 4. To generate the graph 90, the Gaussian mixture model is applied (e.g., by the controller 16) to the raw data points 58 without or prior to data binning. As shown, application of the Gaussian mixture model to the data points 58 may result in the first cluster 82 associated with lower blood pressures and the second cluster 84 associated with higher blood pressures. In the illustrated graph 90, the first cluster 82 is marked by a first set of ellipsoids 92, and the second cluster 84 is marked by a second set of ellipsoids 94. As discussed above, the controller 16 may evaluate the clusters 82, 84 (e.g., evaluate blood pressures within the clusters 82, 84, etc.). For example, in the illustrated embodiment, the controller 16 may evaluate the clusters 82, 84 to determine that the first cluster 82 corresponds to the lower impaired autoregulation zone 62, and the second cluster 84 corresponds to the intact autoregulation zone 60. Furthermore, the controller 16 may determine a boundary 86 between the clusters 82, 84, and may determine that the boundary 86 corresponds to the LLA. In the illustrated embodiment, the boundary 86 is located at a midpoint between the clusters 82, 84 (e.g., between adjacent edges of the clusters 82, 84). In some embodiments, the boundary 86 may be located at an edge of the first cluster 82 associated with the intact autoregulation zone 60 or between the midpoint and the edge of the first cluster 82, for example.

As discussed above, in some embodiments, the controller 16 may be configured to provide an output indicative of the clusters 82, 84 and/or the boundary 86. For example, in some embodiments, the controller 16 may be configured to provide the graph 90 or a similar graphical representation of the clusters 82, 84 and/or the sets of ellipsoids 92, 94 on a display (e.g., via the output device 18). In some embodiments, the controller 16 may be configured provide markers (e.g., boxes or boundaries) about each of the clusters 82, 84 on a display of the graph 90 to facilitate visualization of the clusters 82, 84 and/or the autoregulation zones derived from the clusters 82, 84. The controller 16 may be configured to provide a suitable picture, representation, and/or image (e.g., via the output device 18) depicting one or more of the various autoregulation zones, the LLA, and/or the ULA derived from the clusters 82, 84 and/or the boundary 86.

As shown, the centroid 88 (e.g., a mean or average across all points in the cluster) of the second cluster 84 corresponding to the intact autoregulation zone 60 may be identified (e.g., by the controller 16). In some embodiments, the centroid 88 may be used (e.g., by the controller 16) to generate a target blood pressure for the patient. As discussed above, the target blood pressure may be used by a healthcare provider or by an automated blood pressure control device to manage the patient's blood pressure. In some embodiments, as discussed above, the centroid 89 of a cluster associated with one of the impaired autoregulation zones (e.g., the lower impaired autoregulation zone 62 or the higher impaired autoregulation zone 64) may be identified by the controller 16.

Although a k-means clustering algorithm and a Gaussian mixture model are provided as examples in FIGS. 5 and 6, respectively, it should be understood that any suitable clustering and/or data segmentation algorithms may be utilized to identify clusters of data points 58 that are indicative of the autoregulation zones. For example, the controller 16 may be configured to apply the k-means clustering algorithm, a density-based spatial clustering of applications with noise (DBSCAN) clustering algorithm, principal component analysis (PCA), independent component analysis (ICA), linear discriminant analysis (LDA), learning vector quantization (LVQ), a self-organizing map (SOM or Kohonen net), and/or a Gaussian mixture model to identify clusters of data points 58, which may then be utilized to determine the autoregulation zones, the LLA, the ULA, the target blood pressure, or the like.

Figure 7:
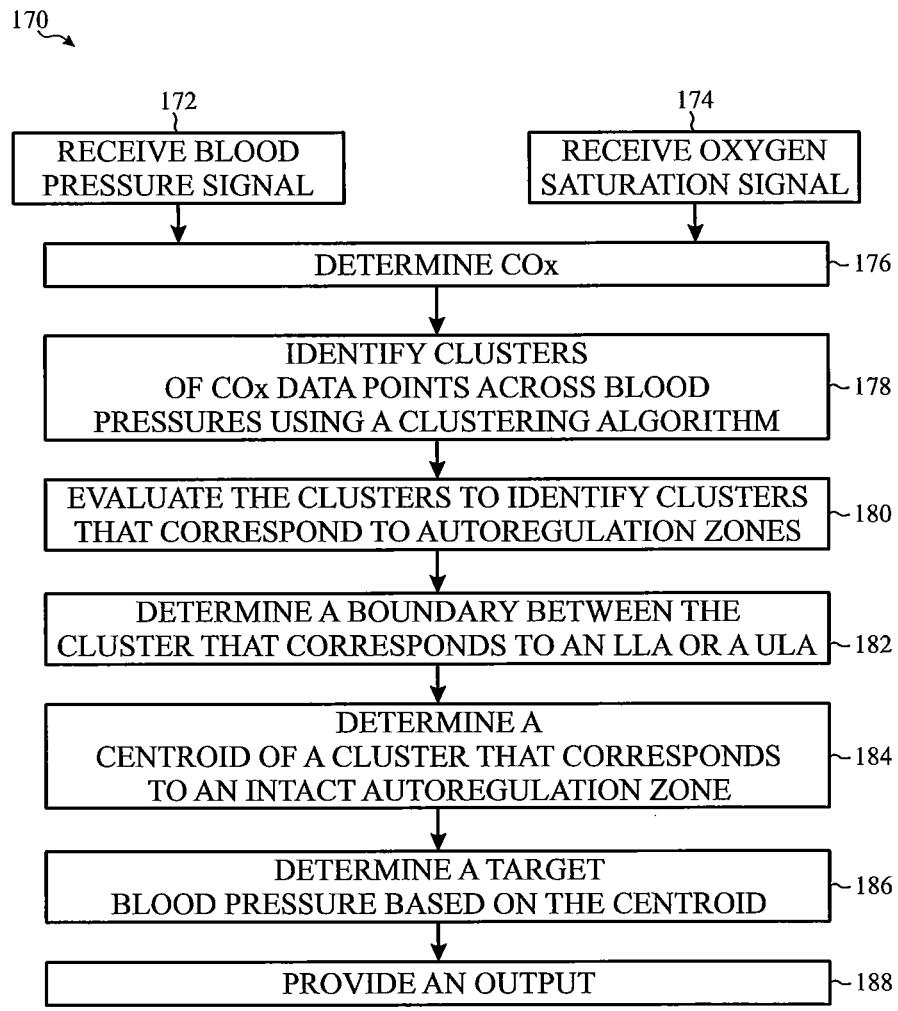
FIG. 7 is a process flow diagram of an embodiment of a method for determining autoregulation zones and a target blood pressure of a patient.

FIG. 7 is a process flow diagram of an embodiment of a method 170 of monitoring autoregulation. The method 170 includes various steps represented by blocks. The method 170 may be performed as an automated procedure by a system, such as system 10. Although the flow chart illustrates the steps in a certain sequence, it should be understood that the steps may be performed in any suitable order, certain steps may be carried out simultaneously, and/or certain steps may be omitted, where appropriate. Further, certain steps or portions of the method 170 may be performed by separate devices. For example, a first portion of the method 170 may be performed by the controller 16, while a second portion of the method 170 may be performed by the sensor 14. In addition, insofar as steps of the method disclosed herein are applied to the received signals, it should be understood that the received signals may be raw signals or processed signals. That is, the method 170 may be applied to an output of the received signals.

In step 172, the controller 16 may receive the blood pressure signal (e.g., arterial blood pressure signal). In some embodiments, the controller 16 may receive the blood pressure signal from the blood pressure sensor 12, as set forth above. In step 174, the controller 16 may receive the oxygen saturation signal. In some embodiments, the controller 16 may receive the oxygen saturation signal from the oxygen saturation sensor 14, as set forth above. In step 176, the controller 16 may determine the COx based on the linear correlation between blood pressure measurements of the blood pressure signal and the oxygen saturation measurements of the oxygen saturation signal.

In step 178, the controller 16 may identify clusters of COx data points (e.g., raw data points 58) across blood pressures using any of a variety of clustering techniques or clustering algorithms, such as the k-means clustering algorithm, a density-based spatial clustering of applications with noise (DBSCAN) clustering algorithm, principal component analysis (PCA), independent component analysis (ICA), linear discriminant analysis (LDA), learning vector quantization (LVQ), a self-organizing map (SOM or Kohonen net), and/or a Gaussian mixture model, or any other suitable clustering technique. Application of the clustering algorithm to the data points 58 may result in one or more clusters of data points 58 (e.g., clusters 82, 84). As discussed above, in some embodiments, the controller 16 may automatically initiate the process of clustering the data points 58 using the clustering algorithm in response to receipt or determination of a predetermined number of data points 58 and/or after a predetermined time period. In some embodiments, the controller 16 may automatically update the clusters during the monitoring session, such as every 15, 30, 60, or 90 seconds.

In step 180, the controller 16 may evaluate the clusters (e.g., clusters 82, 84) to determine clusters that correspond to the various autoregulation zones, as discussed above with respect to FIG. 5, for example. In step 182, the controller 16 may determine the boundary 86 between the clusters (e.g., clusters 82, 84), and may determine that the boundary 86 corresponds to the LLA or the ULA, as discussed above.

In step 184, the controller 16 may determine the centroid 88 of a cluster (e.g., cluster 84) that corresponds to the intact autoregulation zone 60. In step 186, the controller 16 may determine a target blood pressure based on the centroid 88. For example, in some embodiments, a blood pressure value corresponding to the centroid 88 may be the target blood pressure value. In some embodiments, the target blood pressure may be a range of blood pressures about the centroid 88 (e.g., 1, 2, 3, 4, 5, or more percent about the centroid 88 or 1, 5, 10 mmHg about the centroid 88). As discussed above, in some embodiments, the target blood pressure may represent a blood pressure value or a range of values at which the patient's autoregulation function is greatest and/or may be useful for clinical management of a patient's blood pressure. As discussed above, in some embodiments, the controller 16 may be configured to determine the centroid 89 of a cluster (e.g., cluster 82) that corresponds to an impaired autoregulation zone 62, 64 to facilitate patient monitoring. In some embodiments, the controller 16 may automatically update the centroid 88, 89 and/or the target blood pressure during the monitoring session, such as every 15, 30, 60, or 90 seconds.

In step 188, the controller 16 may provide an output (e.g., to the output device 18) related to autoregulation. In particular, the controller 16 may provide an output indicative of the clusters, the boundary, the target blood pressure, the autoregulation zones, the LLA, the ULA, and/or the autoregulation status of the patient, for example. As noted above, the output device 18 may be configured to provide a visual and/or audible indication of the patient's autoregulation status, autoregulation zones, and/or the target blood pressure as determined and/or provided by the controller 16. In some embodiments, the controller 16 may only output (e.g., via the output device 18) information related to the clusters and/or the target blood pressure once the controller 16, using the clustering algorithm, identifies at least two distinct clusters of data points 58. For example, the controller 16 may cause display of information indicative of the clusters, the boundary, the target blood pressure, the autoregulation zones, the LLA, the ULA, and/or the autoregulation status, in response to identification of at least two distinct clusters of data points 58 by the controller 16.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A system configured to monitor autoregulation, the system comprising:
   a medical sensor configured to generate a regional oxygen saturation signal indicative of a blood oxygen saturation of a patient;
   a controller comprising a processor configured to:
      receive the regional oxygen saturation signal and a blood pressure signal indicative of a blood pressure of the patient;
      determine a cerebral oximetry index (COx) based on the blood pressure signal and the regional oxygen saturation signal;
      determine, using a data clustering algorithm, a plurality of clusters, each cluster of the plurality of clusters comprising COx data points over a range of blood pressures, the COx data points corresponding to the determined COx;
      identify a first cluster of the plurality of clusters that corresponds to an intact autoregulation zone for the patient; and
      provide a first output indicative of the intact autoregulation zone for the patient.

2. The system of claim 1, wherein the processor is configured to identify a second cluster of the plurality of clusters that corresponds to an impaired autoregulation zone for the patient and to provide a second output indicative of the impaired autoregulation zone for the patient.

3. The system of claim 1, wherein the processor is configured to identify a boundary between the first cluster and a second cluster of the plurality of clusters and to provide a second output indicative of the boundary.

4. The system of claim 1, wherein the processor is configured to apply the data clustering algorithm in response to determination of a threshold number of COx data points.

5. The system of claim 1, wherein the data clustering algorithm comprises a k-means clustering algorithm.

6. The system of claim 1, wherein the data clustering algorithm comprises a Gaussian mixture model.

7. The system of claim 1, wherein the data clustering algorithm comprises one or more of a density-based spatial clustering of applications with noise (DBSCAN) clustering algorithm, principal component analysis (PCA), independent component analysis (ICA), linear discriminant analysis (LDA), learning vector quantization (LVQ), a self-organizing map (SOM or Kohonen net), or any combination thereof.

8. The system of claim 1, wherein the processor is configured to:
   identify a centroid of the first cluster; and
   determine a target blood pressure based on the centroid of the first cluster.

9. The system of claim 1, further comprising a blood pressure sensor configured to generate the blood pressure signal.

10. A system configured to monitor autoregulation of a patient, the system comprising:
   a controller comprising a processor configured to:
      receive a regional oxygen saturation signal and a blood pressure signal from one or more medical sensors;
      determine a cerebral oximetry index (COx) based on the blood pressure signal and the regional oxygen saturation signal;
      determine, using a data clustering algorithm, a plurality of clusters, each cluster of the plurality of clusters comprising COx data points over a range of blood pressures, the COx data points corresponding to the determined COx; and
      identify a first cluster of the of the plurality of clusters that corresponds to an intact autoregulation zone for the patient.

11. The system of claim 10, wherein the processor is configured to:
   identify a centroid of the first cluster; and
   determine a target blood pressure based on the centroid of the first cluster.

12. The system of claim 10, wherein the data clustering algorithm comprises one or more of a k-means clustering algorithm, a Gaussian mixture model, a density-based spatial clustering of applications with noise (DBSCAN) clustering algorithm, principal component analysis (PCA), independent component analysis (ICA), linear discriminant analysis (LDA), learning vector quantization (LVQ), a self-organizing map (SOM or Kohonen net), or any combination thereof.

13. The system of claim 10, wherein the processor is configured to provide an output indicative of the intact autoregulation zone for the patient.

14. A method of monitoring autoregulation, the method comprising:
receiving, by a processor and from one or more medical sensors, a regional oxygen saturation signal indicative of blood oxygen saturation of a patient, and a blood pressure signal indicative of blood pressure of the patient;
determining, by the processor, a cerebral oximetry index (COx) based on the blood pressure signal and the regional oxygen saturation signal;
determining, by the processor, using a data clustering algorithm, a plurality of clusters, each cluster of the plurality of clusters comprising COx data points over a range of blood pressures, the COx data points corresponding to the determined COx; and
identifying, by the processor a first cluster of the plurality of clusters that corresponds to an intact autoregulation zone for the patient.

15. The method of claim 14, comprising providing, by the processor, an output indicative of the intact autoregulation zone for the patient.

16. The method of claim 14, comprising identifying, by the processor, a second cluster of the plurality of clusters that corresponds to an impaired autoregulation zone for the patient and providing an output indicative of the impaired autoregulation zone for the patient.

17. The method of claim 14, wherein identifying the first cluster using the data clustering algorithm comprises identifying the first cluster in response to determining a threshold number of COx data points.

18. The method of claim 14, wherein the data clustering algorithm comprises one or more of a k-means clustering algorithm, a Gaussian mixture model, a density-based spatial clustering of applications with noise (DBSCAN) clustering algorithm, principal component analysis (PCA), independent component analysis (ICA), linear discriminant analysis (LDA), learning vector quantization (LVQ), a self-organizing map (SOM or Kohonen net), or any combination thereof.

19. The method of claim 14, comprising:
identifying a centroid of the first cluster; and
determining, by the processor, a target blood pressure based on the centroid of the first cluster.

20. The method of claim 19, comprising providing, by the processor, an output indicative of the target blood pressure.

* * * * *